The United States Patent [19]

Nüsslein et al.

[11] 4,209,627
[45] Jun. 24, 1980

[54] 2-(DIMETHYLCARBAMOYLIMINO)-1,3,4-THIADIAZOLINE-3-CARBOXYLIC ACID ESTER DERIVATIVES

[75] Inventors: Ludwig Nüsslein; Friedrich Arndt, both of Berlin, Fed. Rep. of Germany

[73] Assignee: Schering AG, Berlin and Bergkamen, Fed. Rep. of Germany

[21] Appl. No.: 835,529

[22] Filed: Sep. 22, 1977

[30] Foreign Application Priority Data

Sep. 30, 1976 [DE] Fed. Rep. of Germany ....... 2644426

[51] Int. Cl.² .................... A01N 9/12; C07D 285/12
[52] U.S. Cl. ....................... 548/130; 71/86; 71/90; 260/463
[58] Field of Search ..................... 260/306.8 D; 71/90

[56] References Cited
U.S. PATENT DOCUMENTS 3,522,267  7/1970  Duerr et al. .............. 260/306.8 D
3,565,901  2/1971  Cebalo ........................ 260/299
3,840,551  10/1974  Sasse et al. .............. 260/306.8 D
3,954,785  5/1976  Metzger et al. ................ 71/90

Primary Examiner—Alton D. Rollins
Attorney, Agent, or Firm—Michael J. Striker

[57] ABSTRACT 2-(Dimethylcarbamoylimino)-1,3,4-thiadiazoline-3-carboxylic acid ester derivative of the formula

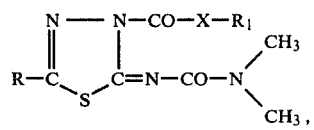

in which R is an aliphatic hydrocarbon and $R_1$ is an aliphatic hydrocarbon, a halogenated aliphatic hydrocarbon, an aromatic hydrocarbon, a substituted aromatic hydrocarbon, an aliphatic-aromatic hydrocarbon or a substituted aliphatic-aromatic hydrocarbon and X is oxygen or sulfur. The compounds have a high herbicidal activity against weeds.

3 Claims, No Drawings

2-(DIMETHYLCARBAMOYLIMINO)-1,3,4-THIADIAZOLINE-3-CARBOXYLIC ACID ESTER DERIVATIVES

BACKGROUND OF THE INVENTION

The invention relates to 2-(dimethylcarbamoylimino)-1,3,4-thiadiazoline-3-carboxylic acid ester derivatives.

1-(1,3,4-thiadiazol-2-yl)-urea derivatives with herbicidal activity have become known from German published applications DT-OS 1 816 694, DT-OS 1 901 672, and DT-OS 2 118 520. These herbicidal agents, however, have the shortcoming of a comparatively low activity against weeds.

It is therefore an object of the present invention to provide for an agent which has a superior herbicidal activity against this kind of plant growth.

SUMMARY OF THE INVENTION

This object is solved by a 2-(dimethylcarbamoylimino)-1,3,4-thiadiazoline-3-carboxylic acid ester derivative of the formula

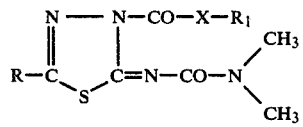

in which R is an aliphatic hydrocarbon and $R_1$ is an aliphatic hydrocarbon, a halogenated aliphatic hydrocarbon, an aromatic hydrocarbon, a substituted aromatic hydrocarbon, an aliphatic-aromatic hydrocarbon or a substituted aliphatic-aromatic hydrocarbon and X is oxygen or sulfur. The compounds have a high herbicidal activity against weeds.

The compounds of the invention are characterized by a broad spectrum activity both when applied to the ground and to the leaves. They can be used against mono- and di-cotyl weeds.

When used both in preemergence and also in postemergence application against weeds in agricultural fields such as Sinapis ssp., *Stellaria media, Senecio vulgaris, Matricaria chamomilla, Ipomoea purpurea, Chrysanthemum segetum, Lamium amplexicaule, Centaurea cyanus, Amaranthus retroflexus, Alopecurus myosuroides, Echinochola crus galli, Setaria italica, Sorghum halepense, Lolium perenne* and other weeds they have surprisingly a higher activity than the mentioned prior art compounds.

To suppress weeds they are normally used in amounts of 0.5 kg of active agent up to 5 kg per 2.5 acres. The compounds of the invention are characterized also by high selectivity against agricultural and other useful plants such as occurred also in wooded areas, ornamental bushes and plantation cultures.

The compounds of the invention may be used either by themselves or intermixed with each other or in mixture with other active agents.

Depending on the particular purpose of use the following herbicidal agents may be employed together with the compounds of the invention. These other agents may be admixed, if desired, immediately prior to use of the inventive compounds:

substituted anilines,
substituted aryloxycarboxylic acids and their salts, esters and amides,
substituted ethers,
substituted arsonic acids and their salts, esters and amides,
substituted benzimidazoles,
substituted benzisothiazoles,
substituted benzthiadiazinode dioxides,
substituted benzoxazines,
substituted benzthiazoles,
substituted benzthiazoles,
substituted biurets,
substituted quinolines,
substituted carbamates,
substituted aliphatic carboxylic acids and their salts, esters and amides,
substituted aromatic carboxylic acids and their salts, esters and amides,
substituted carbamoylalkyl-thio- or dithiophosphates
substituted quinazolines,
substituted cycloalkylamidocarbonylthiol acids and their salts, esters and amides,
substituted cycloalkylcarbonylamido-thiazoles,
substituted dicarboxylic acids and their salts, esters and amides,
substituted dihydrobenzofuranylsulfonates,
substituted disulfides,
substituted dipyridyl salts,
substituted dithiocarbamates,
substituted dithiophosphoric acids and their salts, esters and amides,
substituted urea derivatives,
substituted hexahydro-1H-carbothioates,
substituted hydantoines,
substituted hydrazides,
substituted hydrazonium salts,
substituted isoxazolpyrimidones,
substituted imidazoles,
substituted isothiazolpyrimidones,
substituted ketones,
substituted naphthoquinones,
substituted aliphatic nitriles,
substituted aromatic nitriles,
substituted oxadiazoles,
substituted oxadiazinones,
substituted oxadiazolidinediones,
substituted oxadiazinediones,
substituted phenols and their salts and esters,
substituted phosphonic acids and their salts, esters and amides,
substituted phosphoniumchlorides,
substituted phosphonalkylglycines,
substituted phosphites,
substituted phosphoric acids and their salts, esters and amides,
substituted piperidines,
substituted pyrazoles,
substituted pyrazolalkylcarboxylic acids and their salts, esters, and amides,
substituted pyrazolium salts,
substituted pyrazoliumalkylsulfates,
substituted pyridazines,
substituted pyridazones,
substituted pyridine-carboxylic acids and their salts, esters and amides,
substituted pyridines,
substituted pyridinecarboxylates,
substituted pyridinones, substituted pyrimidones,
substituted pyrrolidine-carboxylic acids and their salts, esters and amides,
substituted pyrrolidines,
substituted arylsulfonic acids and their salts, esters and amides,
substituted styrenes,
substituted tetrahydro-oxadiazindiones,
substituted tetrahydromethanoindenes,
substituted tetrahydro-diazol-thiones,
substituted tetrahydro-thiadiazine-thiones,
substituted tetrahydro-thiadiazinediones,
substituted thiadiazoles,
substituted aromatic thiocarboxylic acid amides,
substituted thiocarboxylic acids and their salts, esters and amides,
substituted thiolcarbamates,
substituted thiophosphoric acids and their salts, esters and amides,
substituted triazines,
substituted triazoles
substituted uracils, and
substituted urethidindiones.

It is possible to use also other additives, for instance, non-phytotoxic additives which, in case of herbicides result in a synergistic increase of activity, such as, wetting agents, emulsifying agents, solvents and oily additives.

The compounds of the invention or their mixtures are suitably employed in the form of compositions such as powders, dusting agents, granulates, solvents, emulsions, or suspensions. In the composition there may be used a liquid and/or solid carrier material or diluent and, if desired, a wetting agent, adhesion promoting agent, emulsifier, and/or dispersion agent.

Suitable liquid carrier materials are, for instance, water, aliphatic and aromatic hydrocarbons, such as, benzene, toluene, xylene, cyclohexanone, isophorone, dimethylsulfoxide, dimethylformamide, and furthermore mineral oil fractions.

As solid carrier materials there may be used mineral earths, for instance, tonsil, silicagel, talc, kaolin, attaclay, limestone, silicic acid and plant products, for instance flours.

There may also be added surface active agents, for instance, calciumlignosulfonate, polyoxyethylenealkyl, phenyl-ethers, naphthalinesulfonic acids and their salts, phenolsulfonic acid and their salts, formaldehyde condensation products, fatty alcoholsulfates, as well as substituted benzosulfonic acids and their salts.

The proportion of the active agent or agents in the total composition can be varied widely. The compositions for instance may be about 10 to 80% by weight of active agents, about 90 to 20% by weight of liquid or solid carrier materials and, if desired, up to 20% by weight of surface active agents.

The application of the compositions can be effected in conventional form, for instance by using water as the carrier material in a spray composition containing about 100 to 1000 liter of composition per about 2.5 acres. The application of the compositions is possible in the so-called "low-volume" and "ultra-low-volume process" as well as in the form of so-called micro-granulates.

Among the compounds of the invention those have superior activity where in the above formula R is alkyl of 1 to 6 carbon atoms, alkenyl of 2 to 6 carbon atoms or alkinyl of the same carbon atom number, and wherein $R_1$ is alkyl of 1 to 8 carbon atoms, alkenyl or alkinyl of 2 to 8 carbon atoms, halogenated alkyl of 1 to 8 carbon atoms, halogenated alkenyl or alkinyl of 2 to 8 carbon atoms, phenyl or benzyl which may be substituted by halogen, alkyl of 1 to 3 carbon atoms, alkoxy of 1 to 3 carbon atoms or trihalogenoalkyl of 1 to 3 carbon atoms, the substitution being present in 1 or 2 places and being the same or different in the several places.

Most preferred because of their high herbicidal selective activity are those compounds of the invention wherein R is methyl, ethyl, propyl, isopropyl, 2-propenyl, 2-propinyl, butyl, isobutyl, sec.-butyl, tert.-butyl, pentyl, isopentyl, 1-methylbutyl, hexyl or 1,1-dimethylbutyl, and wherein $R_1$ is methyl, ethyl, 2,2,2-trichloroethyl, propyl, isopropyl, 2-propenyl, 2-propinyl, 3-chloropropyl, butyl, isobutyl, sec.-butyl, tert.-butyl, 2-butenyl, pentyl, hexyl, heptyl, octyl, phenyl, chlorophenyl, dichlorophenyl, benzyl, chlorobenzyl, or dichlorobenzyl.

The compounds of the invention which have so far not been described in the literature can be made by different processes:

I. A metal compound of the formula

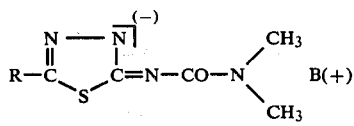

wherein R has the same meaning as in the final product and B is a univalent metal equivalent, preferably lithium, sodium or potassium, is reacted with a halogenoformic acid ester of the formula Hal—CO—X—$R_1$ wherein Hal is halogen and X and $R_1$ have the same meaning as in the product formula. Preferably Hal is chlorine.

II. 1-(1,3,4-thiadiazole-2-yl)-3,3-dimethylurea derivatives of the formula

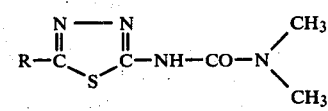

are reacted in the presence of an acid acceptor with a halogenoformic acid ester of the formula

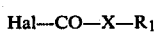

in which two formulas R, $R_1$ and X have the meaning as in the above general formula, and Hal is halogen, preferably chlorine.

In both cases the reaction is carried out at a temperature between 0° and 120° C., preferably at room temperature. The components are used in about equimolar amounts. As reaction medium polar organic solvents are used. Their selection by established principles depends on the type of the metal compound, of halogenoformic acid ester and of acid acceptor. As solvents or suspension agents may be mentioned acid amides such as dimethylformamide; acid nitriles like acetonitrile; ethers like dioxane; ketones like acetone and many others.

As acid acceptors all agents which are conventionally used for such purpose may be employed. Useful are for instance organic bases such as tertiary amines, e.g. triethylamine or N,N-dimethylaniline, pyridine bases or also inorganic bases such as oxides, hydroxides and carbonates of the alkali and alkali earth metals. Liquid bases such as pyridine can also be used at the same time as solvents. The isolation of the formed compounds of the invention is finally effected by distilling off the solvents or by precipitation with water.

The starting products of the above reactions are known or may be produced by obvious processes by way of known reactions.

The following examples will further illustrate the invention:

EXAMPLE 1

17.75 of chloroformic acid-(2-propinyl)-ester are added dropwise by stirring to a suspension of 33.3 g of 5-ethyl-2-(dimethyl-carbamoylimino)-1,3,4-thiadiazoline-3-id, sodium salt in 250 ml acetonitrile. Stirring is then continued for another 3 hours. The reaction mass is subsequently added to six times its amount of icewater. The precipitate that forms is removed by suction and recrystallized from isopropylether.

There are thus obtained 32.7 g (77.3% of the theoretical value) of 5-ethyl-2-(dimethylcarbamoylimino)-1,3,4-thiadiazoline-3-carboxylic acid-(2-propinyl)-ester, m.p. 113° C.

Analysis: Calculated: C 46.80%; H 5.00%; N 19.85%. Obtained: C 46.99%; H 4.99%; N 19.75%.

EXAMPLE 2

12.7 g of 1-(5-tert.-butyl-1,3,4-thiadiazol-2-yl)-3,3-dimethylurea were dissolved in 40 ml pyridine and were reacted dropwise with 8.6 chloroformic ethyl ester. After standing overnight the reaction mixture was added to icewater and neutralized with hydrochloric acid. The precipitated oil was taken up in ether. The ether solution was then dried on magnesium sulfate, the ether was distilled off in a vacuum and the residue was recrystallized from heptane.

Yield: 10.3 g (61.6% of the theoretical value) of 5-tert.-butyl-2-(dimethylcarbamoylimino)-1,3,4-thiadiazoline-3-carboxylic acid ethylester; m.p. 65° C.

Analysis: Calculated: C 47.98%; H 6.71%; N 18.65%. Obtained: C 47.60%; H 6.59%; N 18.64%.

In an analogous manner the following compounds of the invention were made:

| Compound | Physical Constants | |
|---|---|---|
| 5-tert.-butyl-2-(dimethylcarbamoylimino)-1,3,4-thiadiazoline-3-carboxylic acid methylester | m.p. | 84° C. |
| 5-tert.-butyl-2-(dimethylcarbamoylimino)-1,3,4-thiadiazoline-3-thiocarboxylic acid-S-ethylester | m.p. | 68° C. |
| 5-tert.butyl-2-(dimethylcarbamoylimino)-1,3,4-thiadiazoline-3-carboxylic acid butylester | m.p. | 45° C. |
| 5-tert.-butyl-2-(dimethylcarbamoylimino)-1,3,4-thiadiazoline-3-carboxylic acid isopropylester | $n_D 20$ | 1,5267 |
| 5-ethyl-2-(dimethylcarbamoylimino)-1,3,4-thiadiazoline-3-carboxylic acid methylester | m.p. | 125° C. |
| 5-ethyl-2-(dimethylcarbamoylimino)-1,3,4-thiadiazoline-3-carboxylic acid butylester | m.p. | 53° C. |
| 5-ethyl-2-(dimethylcarbamoylimino)-1,3,4-thiadiazoline-3-carboxylic acid ethylester | m.p. | 98° C. |
| 5-butyl-2-(dimethylcarbamoylimino)-1,3,4-thiadiazoline-3-carboxylic acid methylester | m.p. | 95° C. |
| 2(dimethylcarbamoylimino)-5-propyl-1,3,4-thiadiazoline-3-carboxylic acid methylester | m.p. | 116° C. |
| 2-(dimethylcarbamoylimino)-5-methyl-1,3,4-thiadiazoline-3-carboxylic acid methylester | m.p. | 160° C. |
| 2-(dimethylcarbamoylimino)-5-isopropyl-1,3,4-thiadiazoline-3-carboxylic acid methylester | m.p | 84° C. |
| 2-(dimethylcarbamoylimino)-5-isobutyl-1,3,4-thiadiazoline-3-carboxylic acid methylester | m.p. | 70° C. |
| 5-ethyl-2-(dimethylcarbamoylimino)-1,3,4-thiadiazoline-3-carboxylic acid isopropylester | m.p. | 65° C. |

The compounds of the invention are colorless, nonsmelling, oily or crystalline materials which have a low solubility in water but have an increasing solubility in organic solvents in the following sequence: hydrocarbons, halogenated hydrocarbons, ether, ketones, alcohols, carboxylic acids, esters, carboxylic acid nitriles, carboxylic acid amides and many others.

The following examples will further illustrate the use and activity of the compounds of the invention:

EXAMPLE 3

The compounds listed in the following Table I were applied in a hothouse in an amount of 5 kg of active agent per about 2.5 acres suspended in 500 l water per about 2.5 acres to Sinapis sp. and Solanum sp. as test plants in pre- and postemergence application. The application was effected by spraying the plants.

Three weeks after treatment the results were evaluated on a scale from 0=no effect, to 4=total destruction of the plants.

As appears from the table usually a destruction of the test plants was accomplished.

TABLE I

| Compounds | Preemergence application | | Postemergence application | |
|---|---|---|---|---|
| | Sinapis | Solanum | Sinapis | Solanum |
| 5-tert.-butyl-2-(dimethylcarbamoylimino)-1,3,4-thiadiazoline-3-thiocarboxylic acid-S-ethylester | 4 | 4 | 4 | 4 |
| 5-tert.-butyl-2-(dimethylcarbamoylimino)-1,3,4-thiadiazoline-3-carboxylic acid methylester | 4 | 4 | 4 | 4 |
| 5-tert.-butyl-2-(dimethylcarbamoylimino)-1,3,4-thiadiazoline-3-carboxylic acid ethylester | 4 | 4 | 4 | 4 |

TABLE I-continued

| Compounds | Preemergence application | | Postemergence application | |
|---|---|---|---|---|
| | Sinapis | Solanum | Sinapis | Solanum |
| 5-tert.butyl-2-(dimethylcarbamoylimino)-1,3,4-thiadiazoline-3-carboxylic acid butylester | 4 | 4 | 4 | 4 |
| 5-tert.-butyl-2-(dimethylcarbamoylimino)-1,3,4-thiadiazoline-3-carboxylic acid isopropylester | 4 | 4 | 4 | 4 |
| 5-ethyl-2-(dimethylcarbamoylimino)-1,3,4-thiadiazoline-3-carboxylic acid methylester | 4 | 4 | 4 | 4 |
| 5-ethyl-2-(dimethylcarbamoylimino)-1,3,4-thiadiazoline-3-carboxylic acid butylester | 4 | 4 | 4 | 4 |
| 5-ethyl-2-(dimethylcarbamoylimino)-1,3,4-thiadiazoline-3-carboxylic acid ethylester | 4 | 4 | 4 | 4 |
| 5-ethyl-2-(dimethylcarbamoylimino)-1,3,4-thiadiazoline-3-carboxylic acid-(2-propinyl)-ester | 4 | 4 | 4 | 4 |
| 5-butyl-2-(dimethylcarbamoylimino)-1,3,4-thiadiazoline-3-carboxylic acid methylester | — | — | 3 | 3 |
| 2-(dimethylcarbamoylimino)-5-propyl-1,3,4-thiadiazoline-3-carboxylic acid methylester | 4 | 4 | 4 | 4 |
| 2-(dimethylcarbamoylimino)-5-methyl-1,3,4-thiadiazoline-3-carboxylic acid methylester | — | — | — | — |
| 5-isopropyl-2-(dimethylcarbamoylimino)-1,3,4-thiadiazoline-3-carboxylic acid methylester | 4 | 4 | 4 | 4 |
| 5-isobutyl-2-(dimethylcarbamoylimino)-1,3,4-thiadiazoline-3-carboxylic acid methylester | 4 | 4 | 4 | 4 |
| 5-ethyl-2-(dimethylcarbamoylimino)-1,3,4-thiadiazoline-3-carboxylic acid isopropylester | 4 | 4 | 4 | 4 |
| 5-butyl-2-(dimethylcarbamoylimino)-1,3,4-thiadiazoline-3-carboxylic acid benzylester | 3 | 3 | 4 | 3 |

EXAMPLE 4

The plants listed below in Table 2 were treated in a preemergence application in a hothouse with the compounds also listed in the table in amounts of 1 kg of active agent per about 2.5 acres. The compounds were applied to the ground in a uniform manner as aqueous suspensions in 500 liter of water per 2.5 acres.

As appears from the table the compounds of the invention had a higher activity than the comparison compounds. The evaluation was effected on a scale from 0=total destruction, to 10=no injury to the plants.

Table II

| Preemergence application Compounds | kg/ 2.5 acres | Allium | Helianthus | Solanum | Pisum | Triticum | Hordeum | Stellaria | Centaurea | Amaranthus | Polygonum | Avena | Alopecurus | Echinochloa | sorghum |
|---|---|---|---|---|---|---|---|---|---|---|---|---|---|---|---|
| 5-tert.-butyl-2-(dimethylcarbamoylimino)-1,3,4-thiadiazoline-3-carboxylic acid ethylester | 1 | 0 | 0 | 0 | 0 | 0 | 0 | 0 | 0 | 0 | 0 | 0 | 0 | 0 | 0 |
| 5-tert.-butyl-2-(dimethylcarbamoylimino)-1,3,4-thiadiazoline-3-thiocarboxylic acid-S-ethylester | 1 | 0 | 0 | 3 | 0 | 0 | 0 | 0 | 0 | 0 | 0 | 0 | 0 | 0 | 0 |
| 5-tert.-butyl-2-(dimethylcarbamoylimino)-1,3,4-thiadiazoline-3-carboxylic acid ethylester | 1 | 0 | 0 | 0 | 0 | 0 | 0 | 0 | 0 | 0 | 0 | 0 | 0 | 0 | 0 |
| 5-tert.-butyl-2-(dimethylcarbamoylimino)-1,3,4-thiadiazoline-3-carboxylic butylester | 1 | 0 | 0 | 0 | 0 | 0 | 0 | 0 | 0 | 0 | 0 | 0 | 0 | 0 | 0 |

Table II-continued

| Preemergence application Compounds | kg/ 2.5 acres | Al- lium | Heli- anthus | Sol- anum | Pi- sum | Tri- ticum | Hor- deum | Stell- aria | Cen- taurea | Amar- anthus | Poly- gonum | Av- ena | Alo- pec- urus | Ech- ino- chloa | sor- ghum |
|---|---|---|---|---|---|---|---|---|---|---|---|---|---|---|---|
| 5-tert.-butyl-2-(dimethylcar- bamoylimino)-1, 3,4-thiadiazoline- 3-carboxylic isopropylester | 1 | 0 | 0 | 0 | 0 | 0 | 0 | 0 | 0 | 0 | 0 | 0 | 0 | 0 | 0 |
| Comparison compound (German published application 1901672) | | | | | | | | | | | | | | | |
| 1-(5-ethyl-1,3,4- thiadiazole-2- yl)-3,3-di- methylurea | 1 | 7 | 8 | 10 | 9 | 7 | 6 | 5 | 6 | 6 | 4 | 8 | 8 | 9 | 10 |

EXAMPLE 5

The plants listed below in Table III were treated in a postemergence application in a hothouse with the compounds also listed in the table in amounts of 1 kg of active agent per about 2.5 acres. The compounds were sprayed onto the plants as aqueous suspensions in 500 liter water per about 2.5 acres in a uniform manner.

The evaluation 3 weeks after treatment showed that the compounds of the invention had a higher activity than the prior art compound. The evaluation was carried out on a scale from 0—total destruction of the plants, to 10=no injury to the plants.

| Compounds | kg/2.5 acres | Tri- ticum | Itur- deum | Oryza | Sor- ghum | Cuc- umis | Sol- anum | Pi- sum | Ipomea | Av- ena | Alo- pec- urus | Ech- ino- chloa |
|---|---|---|---|---|---|---|---|---|---|---|---|---|
| 5-tert.-butyl-2-(dimethylcarbamoyl- imino)-1,3,4-thiadiazoline-3-car- boxylic acid methylester | 1 | 0 | 0 | 0 | 0 | 0 | 0 | 0 | 0 | 0 | 0 | 0 |
| 5-tert.-butyl-2-(dimethylcarbamoyl- imino)-1,3,4-thiadiazoline-3-thio- carboxylic acid-S-ethylester | 1 | 0 | 0 | 0 | 0 | 0 | 0 | 0 | 0 | 0 | 0 | 0 |
| 5-tert.-butyl-2-(dimethylcarbamoyl- imino)-1,3,4-thiadiazoline-3-car- boxylic acid ethylester | 1 | 0 | 0 | 0 | 0 | 0 | 0 | 0 | 0 | 0 | 0 | 0 |
| 5-tert.-butyl-2-(dimethylcarbamoyl- imino)-1,3,4-thiadiazoline-3-car- boxylic acid isopropylester | 1 | 0 | 0 | 0 | 0 | 0 | 0 | 0 | 0 | 0 | 0 | |
| Comparison compound (German published application 1 901 672) | | | | | | | | | | | | |
| 1-(5-ethyl-1,3,4-thiadiazole-2-yl)- 3,3-dimethyl-urea | 1 | 8 | 5 | 6 | 6 | 8 | 8 | 5 | 8 | 2 | 3 | 5 |

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A compound of the general formula

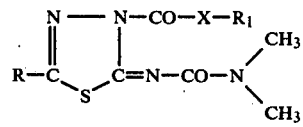

wherein R is alkyl of 1 to 6 carbon atoms, alkenyl or alkinyl of 2 to 6 carbon atoms; $R_1$ is alkinyl of 2 to 8 carbon atoms, or halogenated alkinyl of 2 to 8 carbon atoms, and X is oxygen.

2. The compound of claim 1 which is 5-ethyl-2-(dimethylcarbamoylimino)-1,3,4-thiadiazoline-3-carboxylic acid-(2-propinyl)-ester.

3. The compound 5-t-butyl-2-(dimethylcarbamoylimino)-1,3,4-thiadiazoline-3-thiocarboxylic acid-S-ethylester.

* * * * *